United States Patent [19]

Hwang

[11] Patent Number: 5,374,271
[45] Date of Patent: Dec. 20, 1994

[54] DOUBLE NAIL GUIDING SYSTEM FOR TARGETING OF DISTAL SCREW HOLES OF INTERLOCKING NAILS

[76] Inventor: Chi-Yuan Hwang, 23-42, Lane 556, Sec. 1, Chung-Shan Road, Chang-Hua City, Taiwan, Prov. of China

[21] Appl. No.: 21,563

[22] Filed: Feb. 24, 1993

[51] Int. Cl.⁵ .............................. A61B 17/58
[52] U.S. Cl. ............................. 606/86; 606/62; 606/64; 606/67; 606/72
[58] Field of Search ............ 606/53, 60, 62, 64, 606/67, 72, 86, 87, 88, 96, 98, 104

[56] References Cited

U.S. PATENT DOCUMENTS

| | | | |
|---|---|---|---|
| 4,622,959 | 11/1986 | Marcus | 606/64 |
| 4,913,137 | 4/1990 | Azer et al. | 606/64 |
| 5,176,681 | 1/1993 | Lawes et al. | 606/64 |
| 5,207,682 | 5/1993 | Cripe | 606/98 |
| 5,228,459 | 7/1993 | Caspari et al. | 606/86 |

FOREIGN PATENT DOCUMENTS

| | | | |
|---|---|---|---|
| 0250255 | 10/1987 | Germany | 606/96 |
| 2258154 | 2/1993 | United Kingdom | 606/86 |
| 1581300 | 7/1990 | U.S.S.R. | 606/87 |

Primary Examiner—Stephen C. Pellegrino
Assistant Examiner—Jeffrey A. Schmidt
Attorney, Agent, or Firm—Beveridge, DeGrandi, Weilacher & Young

[57] ABSTRACT

A double nail guiding system for stabilizing broken bones includes a twin jig, first and second interlocking nails extending from the twin jig, wherein each interlocking nail defines a channel along a longitudinal axis thereof. The interlocking nails also include a distal portion which includes at least one hole. A centric or eccentric guiding pipe, including a channel in the center, extends through the first interlocking nail in a direction toward the second interlocking nail. A K-wire is inserted into the channel in the guiding pipe, such that the K-wire extends through the guiding pipe and through the hole defined in the second interlocking nail which is in the bone being stabilized. A guide probe is inserted into the channel in the second interlocking nail (which is in the bone) toward the distal portion thereof. In this manner, alignment of the hole in the distal portion of the first interlocking nail and the hole in the distal portion of the second interlocking nail is confirmed by contacting the guide probe with the K-wire. Advantageously, the first interlocking nail and the second interlocking nail are constructed to be of equal length and equal size.

8 Claims, 8 Drawing Sheets

1

DOUBLE NAIL GUIDING SYSTEM FOR TARGETING OF DISTAL SCREW HOLES OF INTERLOCKING NAILS

BACKGROUND OF THE INVENTION

Successful placement of the distal screws into a tibial and femoral interlocking nail without roentgenogram assistance is a technically demanding procedure, because the accuracy of the targeting device included in the original systems requires a time wasting and inaccurate method. Furthermore, the most commonly used technique for distal interlocking screw placement is the freehand method. However, the freehand method still includes the drawbacks of time expenditure and radiation exposure.

Therefore, it is an object of the present invention to provide a new guiding system which may obviate and mitigate the above-mentioned drawbacks.

SUMMARY OF THE INVENTION

This invention relates to a double nail guiding system.

It is the primary object of the present invention to provide a double nail guiding system which includes a combination of two interlocking nails of equal length and/or size for the distal screw targeting procedure.

It is another object of the present invention to provide a double nail guiding system which is simple in structure.

It is still another object of the present invention to provide a double nail guiding system which is easy to adjust during the operation.

It is still another object of the present invention to provide a double nail guiding system which is economical to produce.

It is still another object of the present invention to provide a double nail guiding system which is accurate during the operation.

It is still another object of the present invention to provide a double nail guiding system which markedly saves operation time.

It is still another object of the present invention to provide a double nail guiding system which is radiation-free in the process of targeting the distal interlocking screws during the operation.

It is a further object of the present invention to provide a double nail guiding system which can be used for a long time.

Other objects and merits and a fuller understanding of the present invention will be obtained by those having ordinary skill in the art when the following detailed description of the preferred embodiment is read in conjunction with the accompanying drawings.

DETAILED DESCRIPTION OF THE PREFERRED EMBODIMENT

Figure 1:
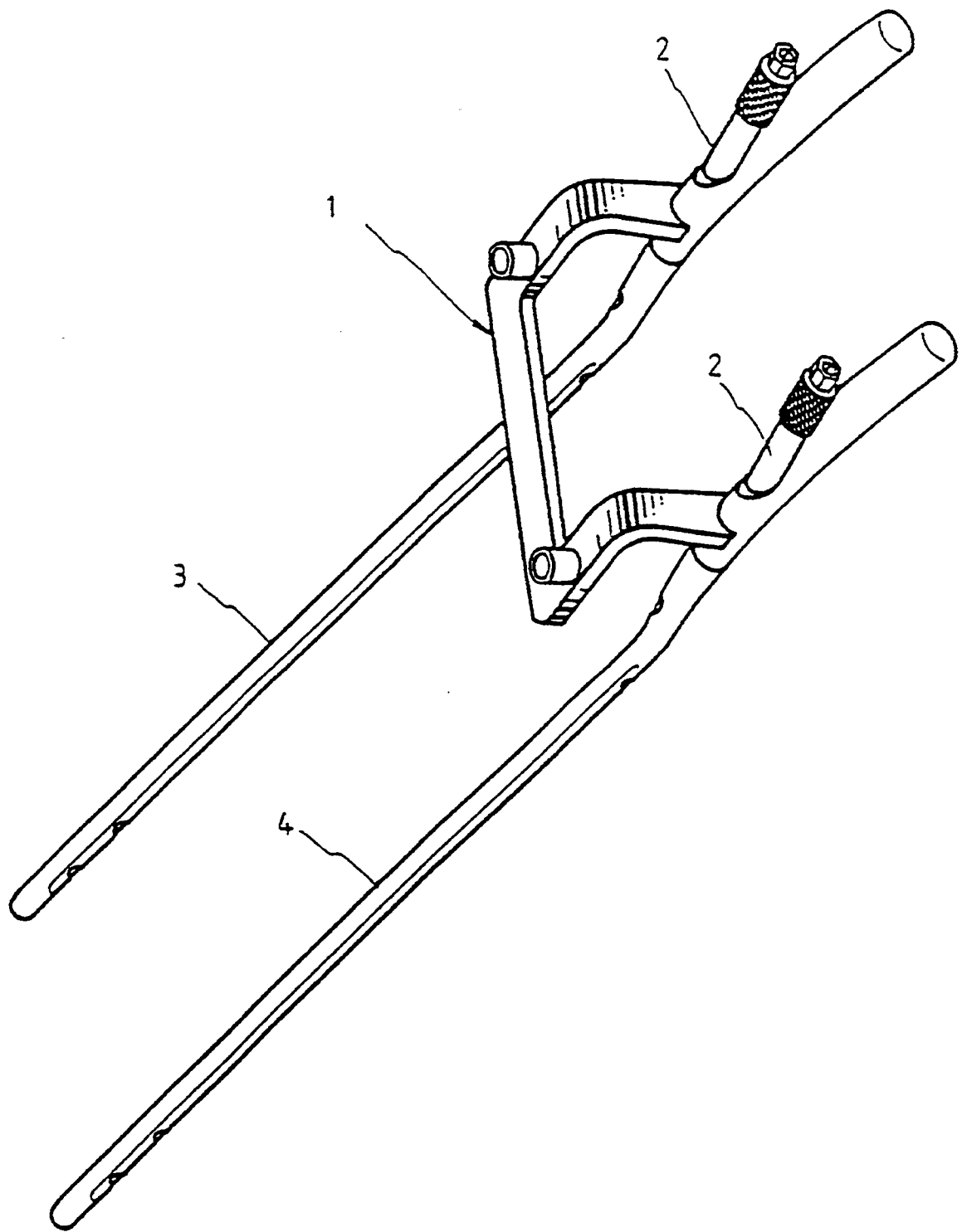
FIG. 1 is a perspective view of a double nail guiding system for targeting of distal screw holes of the tibia interlocking nail according to the present invention.

With reference to the drawings, and in particular to FIG. 1 thereof, the double nail guiding system in accordance with the invention includes a tibial twin jig (1) which may be connected to two nails (3,4) of equal length with two separate holding screws (2). The nail that will be driven into the fractured tibia is called the "true nail". The other nail at the medial border of the leg is called the "guiding nail" based on its use as a guide. For example, in right tibia unstable fractures, the left side interlocking nail (3) of this combination is the true nail which will be inserted into the fractured tibia. The right side nail (4) on the medial side of the leg acts as a guiding nail. Alternatively, in left tibia unstable fractures, the right side nail (4) acts as the true nail, and the left side nail (3) acts as the guiding nail.

Figure 2:
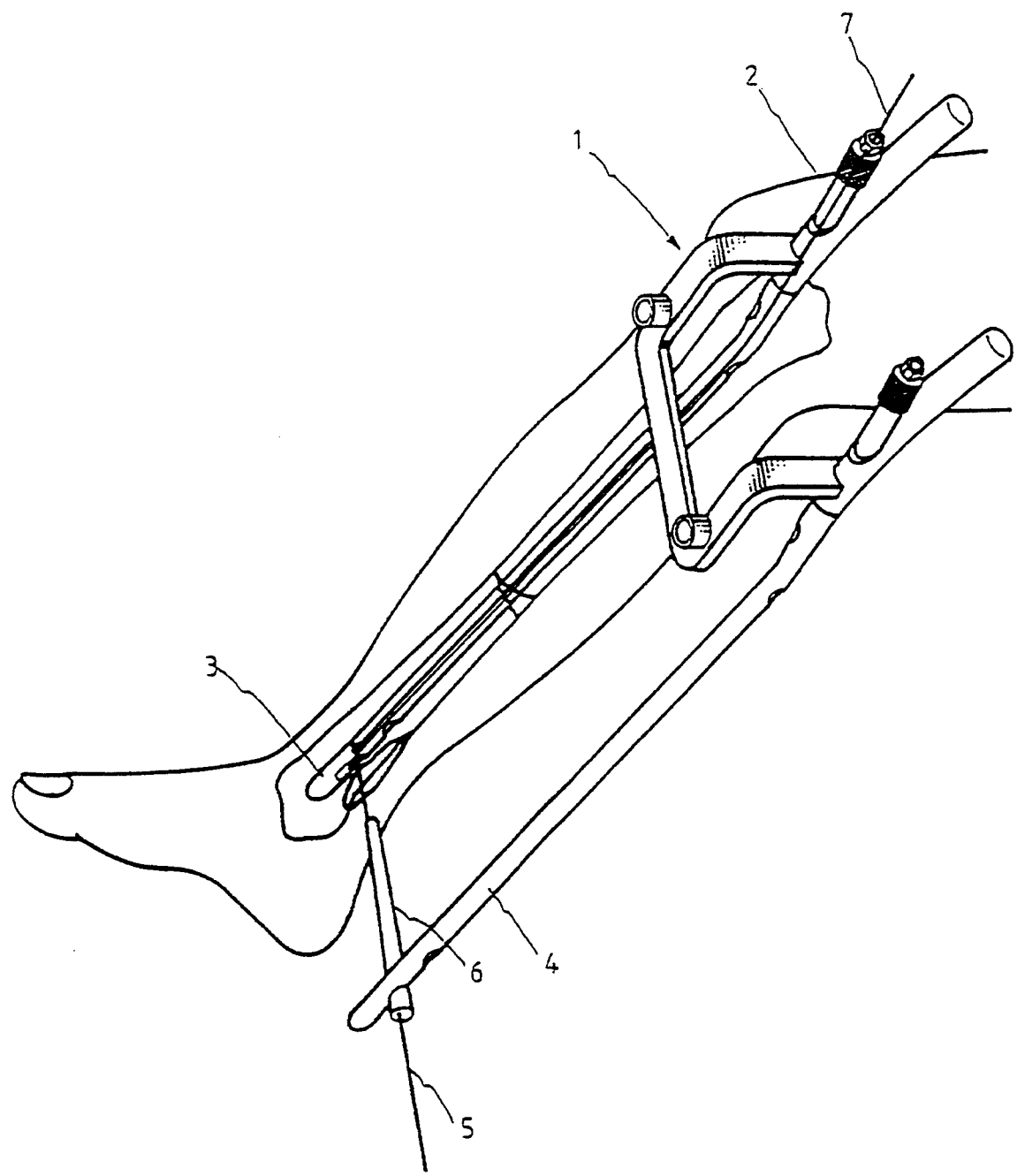
FIG. 2 is a perspective view showing the application of the double nail guiding system in the tibia for targeting the most distal interlocking screw hole.

As shown in FIG. 2, using the double nail guiding system in accordance with the invention, a K-wire (5) and an eccentric guiding pipe (6) are used in targeting the most distal screw hole of the true nail (3) inside the tibia. Due to the fact that the position of the distal screw holes of the tibia interlocking nail may include errors as a result of manufacturing, sets of centric and eccentric pipes are designed to correct these intrinsic errors.

Additionally, a guiding probe (7) is put into the true nail (3) from the proximal end to the distal end to make sure that the K-wire (5) is transfixing through the most distal screw hole of the true nail (3). A metallic sound may be heard when the guiding probe (7) hits the K-wire (5). Thereafter, the K-wire (5) and the guiding pipe (6) are removed.

Figure 3:
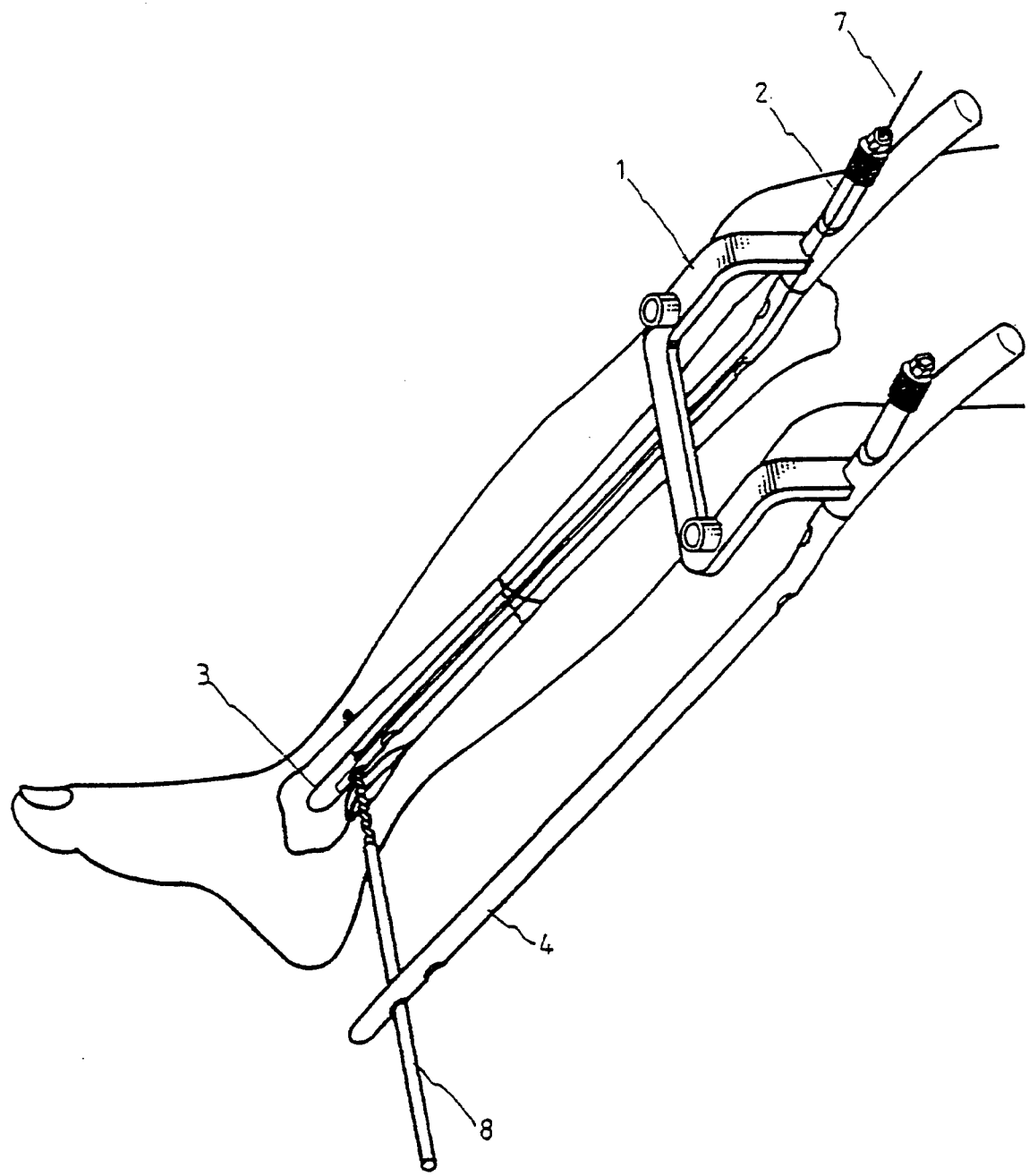
FIG. 3 shows the application of a drill in the most distal screw hole of the double nail guiding system in the tibia.

FIG. 3 shows a drill (8) going through the K-wire (5) pre-drilled cortices. The guiding probe (7) may be used again to make sure that the drill (8) is transfixing the true nail (3). Thereafter, the drill (8) and the guiding nail (4) are removed.

Figure 4:
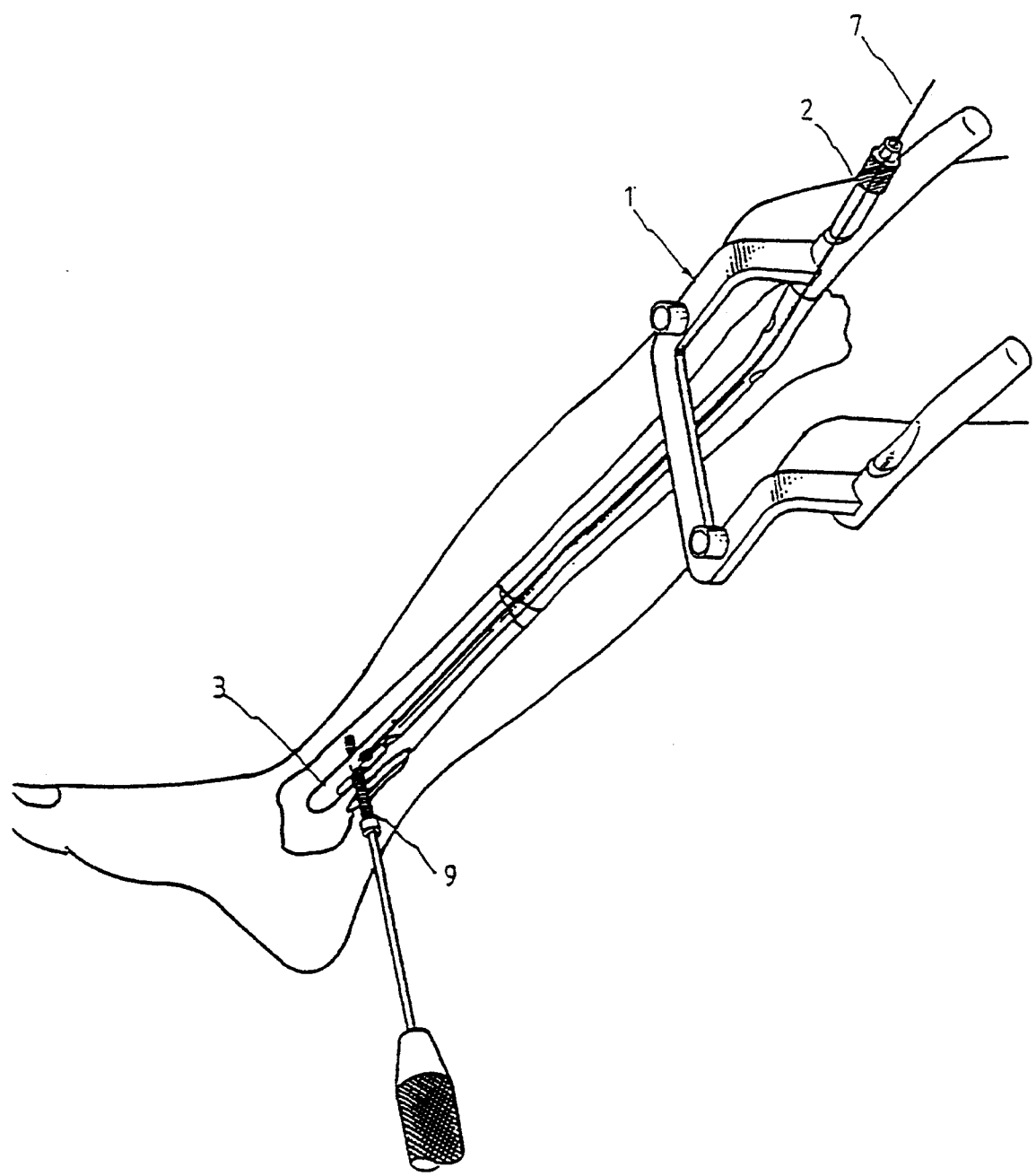
FIG. 4 shows a view illustrating the driving of the transfixing interlocking screw into the most distal screw hole of the double nail guiding system in the tibia.

FIG. 4 shows a screw (9) being driven into the true nail (3). The guiding probe (7) may be used to make sure that the screw (9) is driven at the proper location. No radiation exposure is necessary.

The targeting of the second distal interlocking screw hole of the tibia interlocking nail is performed following the same procedures described above.

Figure 5:
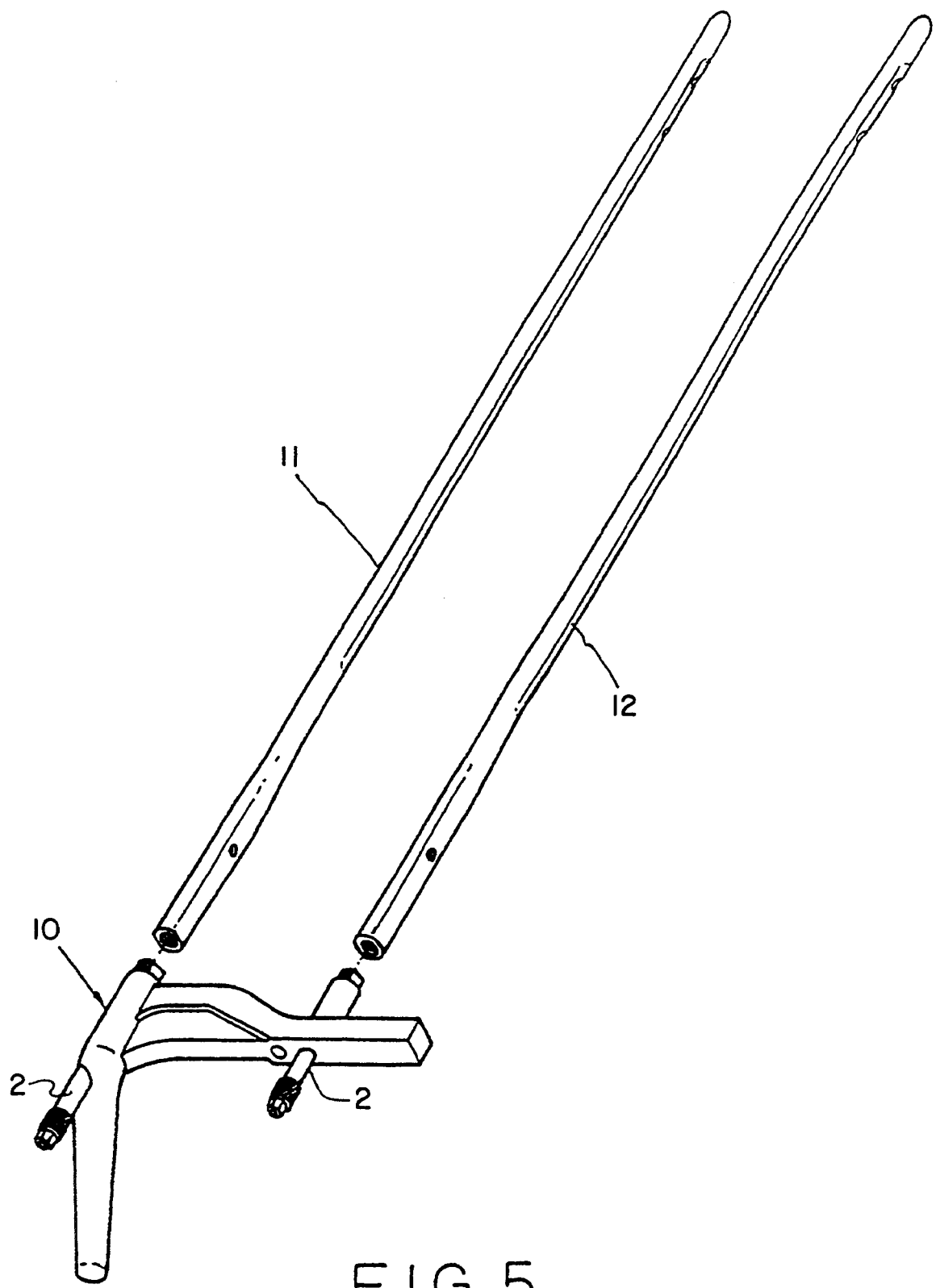
FIG. 5 is an exploded view of a double nail guiding system for targeting of a distal screw hole of the femoral interlocking nail according to the present invention.

FIG. 5 illustrates an exploded view of a femoral twin jig (10) according to the present invention. The femoral twin jig (10) may be connected to two nails (11,12) of equal length with two separate holding screws (2). The nail that will be put into the fractured femur is called the "true nail". The other nail at the lateral border of the thigh is called the "guiding nail" based on its use as a guide. For example, in right femoral unstable fractures, the left side interlocking nail (11) of this combination is the true nail which will be inserted into the fractured femur. The right side nail (12) on the lateral side of the leg acts as the guiding nail. In left femoral unstable fractures, the left side nail (11) still acts as the true nail and the right side nail (12) acts as the guiding nail. Due to the fact that the position of the distal screw holes of the femoral interlocking nail may include errors as a result of manufacturing, sets of eccentric pipes are designed to correct these intrinsic errors.

Figure 6:
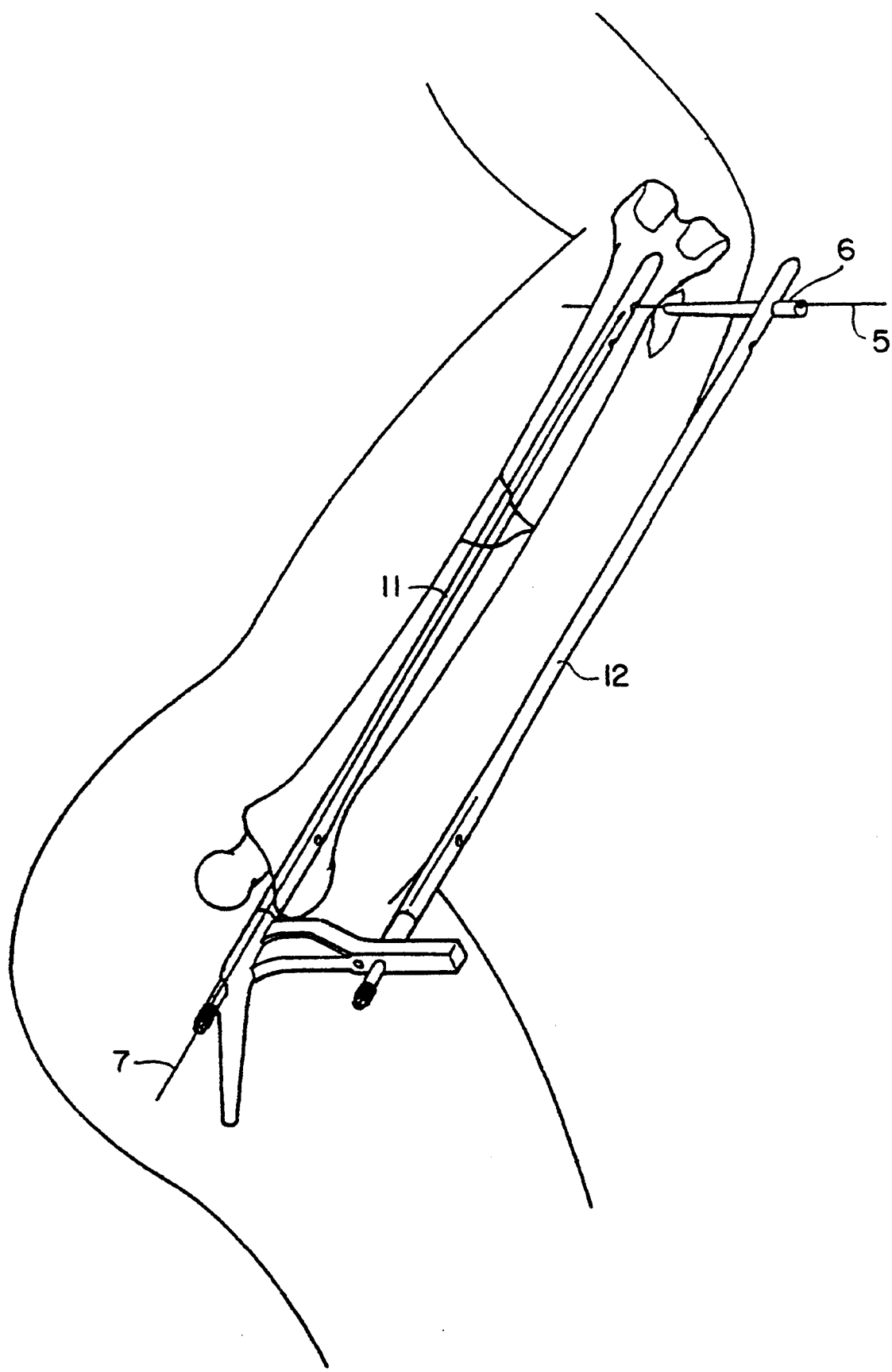
FIG. 6 is a perspective view showing the application of the double nail guiding system in the femur for targeting the most distal interlocking screw hole.

As shown in FIG. 6, using the double nail guiding system in accordance with the invention, a K-wire (5) and an eccentric guiding pipe (6) are used to target the most distal screw hole of the true nail (11) inside the femur. Additionally, a guiding probe (7) is put into the true nail (11) from the proximal end to the distal end to make sure that the K-wire (5) is transfixing through the most distal screw hole of the true nail (11). A metallic sound may be heard when the guiding probe (7) hits the K-wire (5). Thereafter, the K-wire (5) and guiding pipe (6) are removed.

Figure 7:
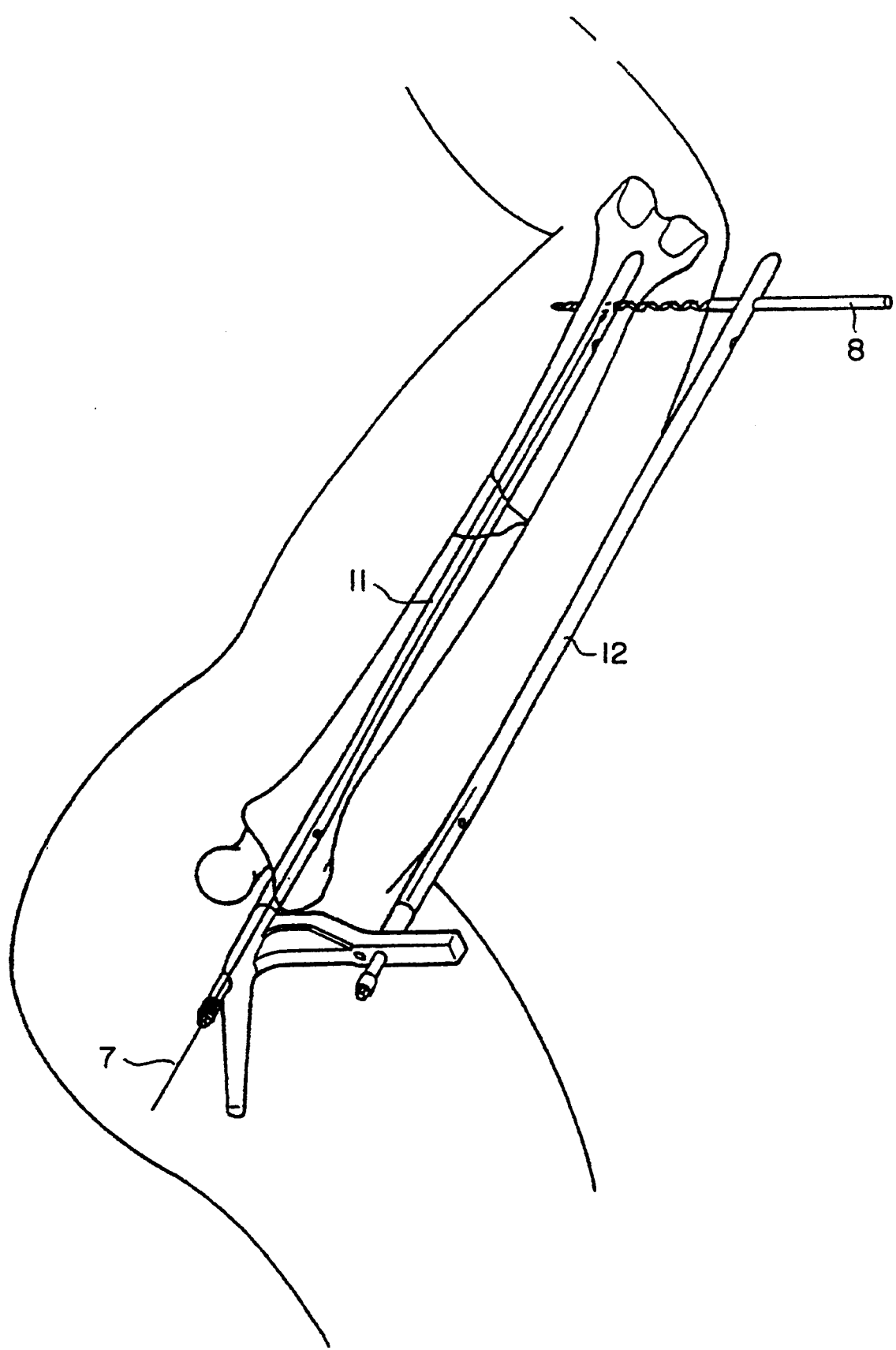
FIG. 7 shows the application of a drill in the most distal screw hole of the double nail guiding system in the femur.

FIG. 7 shows a drill (8) going through the K-wire (5) pre-drilled cortices. The guiding probe (7) may be used again to make sure that the drill (8) is transfixing the true nail. Thereafter, the drill (8) and guiding nail (12) are removed.

Figure 8:
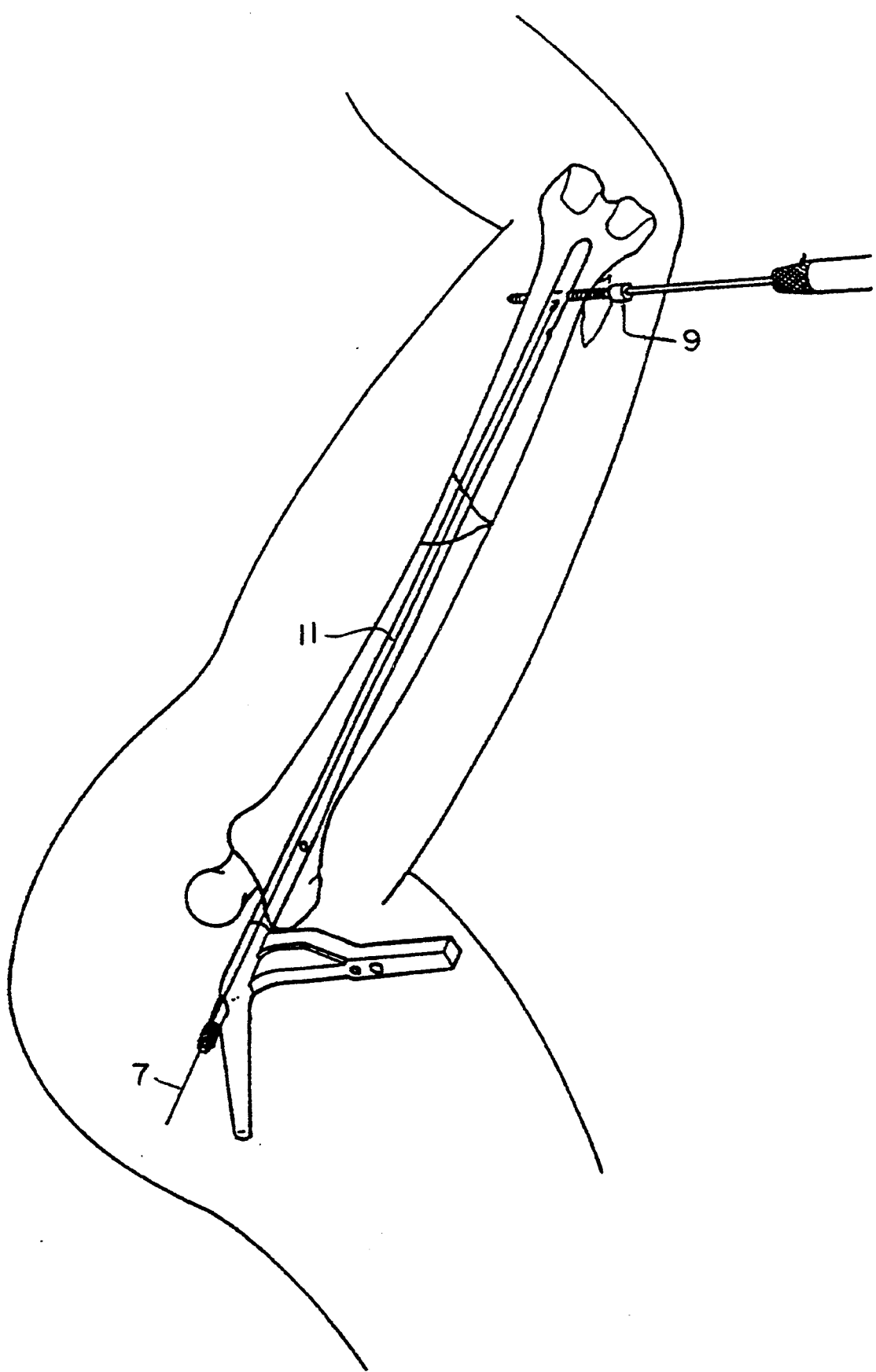
FIG. 8 shows a view illustrating the driving of the transfixing interlocking screw into the most distal screw hole of the double nail guiding system in the femur.

FIG. 8 shows a screw (9) being driven into the true nail (11). The guiding probe (7) may be used to make sure that the screw (9) is driven at the proper location. No radiation exposure is necessary.

The targeting of the second distal interlocking screw hole of the femur interlocking nail is performed following the same procedures described above.

It should be noted, however, that the present invention (DNRG system) may be used for targeting different types of interlocking nails.

The interlocking nails in accordance with the invention may be used for long bone fractures, such as tibia, femur, humerus, radius, ulna, metacarpal and metatarsal fractures.

The application of the present invention is too wide to be mentioned and cannot be all enumerated here in detail. It is understood that the present disclosure is made by way of example only, and that numerous changes in the detail of the construction and combination of parts may be resorted to without departing from the spirit and scope of the invention as hereinafter claimed.

I claim:

1. A double nail guiding system, comprising:
   a twin jig;
   a first interlocking nail extending from the twin jig, wherein the first interlocking nail defines a channel along a longitudinal axis thereof, the first interlocking nail including a distal portion which includes at least one hole defined therein;
   a second interlocking nail extending from the twin jig, wherein the second interlocking nail defines a channel along a longitudinal axis thereof, the second interlocking nail including a distal portion which includes at least one hole defined therein;
   a centric or eccentric guiding pipe defining a channel therethrough, the guiding pipe extending through the first interlocking nail in a direction toward the second interlocking nail;
   a K-wire for inserting into the channel defined in the guiding pipe and extending through the guiding pipe and through the hole defined in the second interlocking nail; and
   a guide probe for inserting into the channel defined in the second interlocking nail toward the distal portion thereof, wherein alignment of the hole in the distal portion of the first interlocking nail and the hole in the distal portion of the second interlocking nail is confirmed by contacting the guide probe with the K-wire.

2. The double nail guiding system according to claim 1, wherein the first interlocking nail and the second interlocking nail are of equal length.

3. The double nail guiding system according to claim 1, wherein the first interlocking nail and the second interlocking nail are of equal size.

4. The double nail guiding system according to claim 1, further comprising holding screws for connecting the first interlocking nail and the second interlocking nail to the twin jig.

5. The double nail guiding system according to claim 1, wherein two holes are defined in the distal portion of the first interlocking nail, and two holes are defined in the distal portion of the second interlocking nail.

6. A double nail guiding system, comprising:
   a twin jig;
   a first interlocking nail extending from the twin jig, wherein the first interlocking nail defines a channel along a longitudinal axis thereof, the first interlocking nail including a distal portion which includes at least one hole defined therein;
   a second interlocking nail extending from the twin jig, wherein the second interlocking nail defines a channel along a longitudinal axis thereof, the second interlocking nail including a distal portion which includes at least one hole defined therein;
   wherein the first interlocking nail and the second interlocking nail are of equal length and size such that when a broken bone is being treated on the right side of a body, the first interlocking nail is used as a true nail and the second interlocking nail is used as a guide nail, and when a broken bone is being treated on the left side of the body, the first interlocking nail is used as the guide nail and the second interlocking nail is used as the true nail;
   a centric or eccentric guiding pipe defining a channel therethrough, the guiding pipe extending through the guide nail in a direction toward the true nail;
   a K-wire for inserting into the channel defined in the guiding pipe and extending through the guiding pipe and through the hole in the true nail; and
   a guide probe for inserting into the channel defined in the true nail toward the distal portion thereof, wherein alignment of the hole in the true nail and the hole in the guide nail is confirmed by contacting the guide probe with the K-wire.

7. The double nail guiding system according to claim 6, further including holding screws for connecting the first interlocking nail and the second interlocking nail to the twin jig.

8. The double nail guiding system according to claim 6, wherein two holes are defined in the distal portion of the first interlocking nail, and two holes are defined in the distal portion of the second interlocking nail.

* * * * *